United States Patent [19]

Weeks

[11] Patent Number: Plant 5,451

[45] Date of Patent: Apr. 30, 1985

[54] ROSE PLANT

[76] Inventor: O. L. Weeks, 926 W. Philadelphia, Ontario, Calif. 91761

[21] Appl. No.: 540,412

[22] Filed: Oct. 11, 1983

[51] Int. Cl.[3] ..... A01H 5/00

[52] U.S. Cl. ..... Plt./14

[58] Field of Search ..... Plt./14–15

*Primary Examiner*—Robert E. Bagwill

*Attorney, Agent, or Firm*—Vincent G. Gioia

[57] ABSTRACT

A new white hybrid tea rose with tannish haze.

1 Drawing Figure

1

The present invention relates to a new and distinct variety of rose plant of the hybrid tea rose class, which was originated by my crossing as seed parent an unpatented, unnamed seedling of my creation and the rose known as "Louisiana" (U.S. Plant Pat. No. 3,719) as pollen parent. The denomination of this new rose is "Chablis".

Among the novel characteristics possessed by this new variety which distinguish it from its parents and all other varieties of which I am aware are its flowers of good form prolifically produced on a vigorous plant and having a general tonality of white coloring with a tannish haze. Asexual reproduction by budding of the new variety as performed in San Bernardino County, Calif., shows that the foregoing and other distinguishing characteristics come true to form and are established and transmitted through succeeding propagations.

The seed parent of the new variety has a distinctly yellow flower coloring in contrast to the off-white coloring of the new variety. The growth habit and foliage of the new variety is also different and superior to the seed parent. The pollen parent, "Louisiana", is also different than the new variety in its foliage and growth habit as well as flower form and coloring.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "158A" is plate 158A of The Royal Horticultural Society Colour Chart.

Parentage: Seedling.

*Seed parent.*—Unnamed, unpatented seedling.

*Pollen parent.*—"Louisiana".

Class: Hybrid Tea.

The following observations are made of specimens grown outdoors in San Bernardino County, Calif., during the month of August.

FLOWER

Blooming habit: Recurrent.

Bud:

(1) *Size.*—Medium.

(2) *Form.*—Pointed.

2

(3) *Color.*—When bud first shows color, before sepals divide, near 145C to D. After sepals divide, buds are chrome yellow 158A.

(4) *Sepals.*—Reach to tip of unopened bud.

(5) *Peduncle.*—Length — medium. Aspect — curved. Strength — medium. Color — near 146C to D.

Bloom:

(1) *Size.*—Average size when fully expanded — about 4 inches.

(2) *Borne.*—Singly and small clusters.

(3) *Form.*—High centered holding form until fully open. At fully open stage petals remain erect.

(4) *Petalage.*—Number of petals under normal conditions — about 40 to 50.

(5) *Color.*—After sepals fall and first petals unfurl, bud appears as deeper toned chrome yellow 158A (almost 159A). As flowers open further, tonality lightens becoming 158B through 158D with deeper tone 158A still visible at flower center. There is also occasional green striping blemish of outer petals. General tonality from a distance is white coloring with a tannish haze.

Petals:

(1) *Texture.*—Medium.

(2) *Appearance.*—Inside and outside velvety.

(3) *Form.*—Acuminate.

(4) *Arrangement.*—Regularly arranged.

(5) *Petaloids in center.*—Few (5 to 10).

(6) *Persistence.13* Spent bloom may retain 2 or 3 petals.

(7) *Fragrance.*—Slight.

(8) *Lasting quality.*—Average lasting quality on plant.

REPRODUCTIVE ORGANS

Stamens, filaments and anthers:

*Arrangement and color.*—Reddish yellow stamens somewhat irregularly arranged around styles.

Pollen:

*Color.*—Yellow.

Styles: Uneven medium length.

Stigmas:

*Color.*—Light yellow.

Hips: None observed.

PLANT

Form: Upright, compact.

Growth: Very vigorous, uniformly branched and neatly contained.

*Height attained.*—About 5 feet.

Foliage: Compound 5 to 7 leaflets.

(1) *Size.*—Large.

(2) *Quantity.*—Abundant.

(3) *Color.*—New foliage: Upper side — near to 46A. Under side — near to 183B to C. Old foliage: Upper side — near 147A. Under side — near to 147C.

(4) *Shape.*—Oval, long pointed.

(5) *Texture.*—Upper side is leathery and under side is satiny.

(6) *Edge.*—Serrate.

(7) *Serration.*—Regular.

(8) *Leaf stem.*—Color — near to 147B. Under side — near 147C.

(9) *Stipules.*—Slightly bearded, medium.

(10) *Resistance to disease.*—Mildew — average.

Wood:

(1) *New wood.*—Color — near 146B to C. Bark — smooth.

(2) *Old wood.*—Color — near 146A to B. Bark — smooth.

Thorns:

(1) *Thorns.*—Quantity (main stalk) — few. On laterals from stalk — average. Form — thin, slight recurve. Length — medium. Color — near 146C to D. Position — irregular.

(2) *Prickles.*—Few on main stem.

Winter hardiness: Needs winter protection in severe climate.

I claim:

1. A new and distinct variety of rose plant of the hybrid tea rose class, substantially as shown and described, characterized particularly by off-white colored flowers of good form borne one to a stem and in small clusters on a vigorous plant and which provides a general tonality of white with a tannish haze.

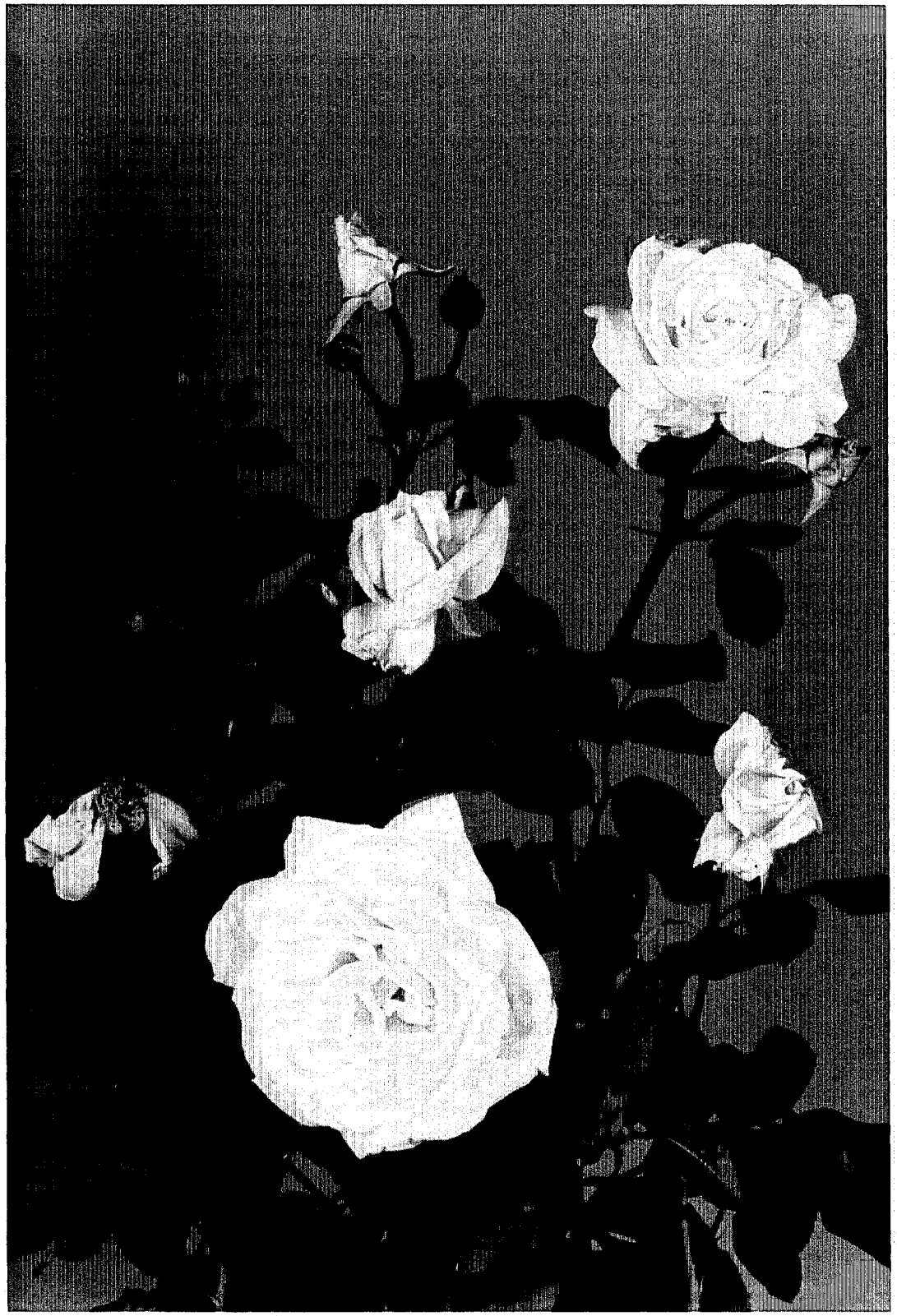

* * * * *